United States Patent [19]

Nelson

[11] Patent Number: 5,759,766
[45] Date of Patent: Jun. 2, 1998

[54] DIAGNOSIS OF SCLERODERMA AND RELATED DISEASES

[75] Inventor: J. Lee Nelson, Seattle, Wash.

[73] Assignee: Fred Hutchinson Cancer Research Center, Seattle, Wash.

[21] Appl. No.: 683,888

[22] Filed: Jul. 19, 1996

Related U.S. Application Data

[60] Provisional application No. 60/001,315 Jul. 21, 1995.

[51] Int. Cl.$^6$ .......................... G01N 33/53; C12Q 1/68; C12P 19/34
[52] U.S. Cl. .................. 435/4; 435/6; 435/7.1; 435/7.21; 435/91.2; 436/501; 436/506; 436/518; 436/63; 436/811; 935/77; 935/78
[58] Field of Search ............ 435/7.1, 6, 4, 91.2, 435/7.21, 811, 405; 436/501, 506, 518, 63; 935/77, 78

[56] References Cited

U.S. PATENT DOCUMENTS

| | | | |
|---|---|---|---|
| 4,550,086 | 10/1985 | Reinherz et al. | 436/506 |
| 4,743,538 | 5/1988 | Zabriskie et al. | 435/7 |
| 5,192,553 | 3/1993 | Boyse et al. | 424/529 |

OTHER PUBLICATIONS

Chosidow et al, Journal of the American Academy of Dermatology (Jan. 1992) 26: 49–55.
Clark et al British Journal Surgery (1 May 1992) 79: 424–426.
Landman–Parker et al, Leukemia (Nov. 1994) 8: 1989–1994.
Colling et al, New England Journal of Medicine (Mar. 1993) 328: 762–765.
Clark et al., "Persistance of Allogeneic Cells in Graft and Host Tissues after Small Bowel Transplantation," *Br. J. Surg.*, 79:424–426 (1992).
Venuat et al., "Fluorescence in situ Hybridization with X and Y DNA Specific Probes for Chimerism Detection in Pulmonary Alveolar Macrophages after Human Sex–Mismatched Allogeneic Bone Marrow Transplantation," *Bone Marrow Transplantation*, 14:177–179 (1994).
Herzenberg et al., "Fetal cells in the Blood of Pregnant Women: Detection and Enrichment by Fluorescence–Activated Cell Sorting", *Proc. Natl. Acad. Sci.*, 76:1453–1455 (Mar., 1979).
Yeoh et al., "Detection of Fetal Cells in Maternal Blood", *Prenatal Diagnosis*, 11:117–123 (1991).
Wessman et al., "Fetal Granulocytes in Maternal Venous Blood Detected by In Situ Hybridization.", *Prenatal Diagnosis*, 12:993–1000 (1992).
Kuwana et al., "The HLA–DR and DQ Genes Control the Autoimmune Response to DNA Topoisomerase I in Systemic Sclerosis (Scleroderma)", *J. Clin. Invest.*, 92:1296–1301 (Sep., 1993).
Simpson et al., "Isolating Fetal Cells From Maternal Blood", *J. Amer. Med. Assoc.*, 270:2357–2361 (Nov., 1993).
Demetris et al., "Hematolymphoid Cell Trafficking, Microchimerism, and GVH Reactions After Liver, Bone Marrow, and Heart Transplantation", *Transplantation Proceedings*, 25:3337–3344 (Dec., 1993).
Sargent et al., "Isolating and Analyzing Fetal Leukocytes in Maternal Blood", *Ann. NY Acad. Sci.*, 147–153 (1994).

*Primary Examiner*—Carla J. Myers
*Attorney, Agent, or Firm*—Townsend and Townsend and Crew LLP

[57] ABSTRACT

Allogeneic cells are removed from an individual predisposed to or suffering from scleroderma or related diseases, thereby treating the disease and inhibiting or preventing its recurrence. Allogeneic cells are identified in the individual and treatment tailored to remove such cells, in vivo or ex vivo, from the individual by cell separation or cytotoxic agents.

9 Claims, No Drawings

DIAGNOSIS OF SCLERODERMA AND RELATED DISEASES

GOVERNMENT SUPPORT

The U.S. government may have certain rights in the invention pursuant to Grant Nos. AR39282 and AI 38583 received from the U.S. National Institutes of Health.

This application claims the benefit of U.S. provisional application Ser. No. 60/001,315, filed Jul. 21, 1995.

BACKGROUND OF THE INVENTION

Women are more frequently affected by autoimmune diseases (Rose et al., *Immunol. Today* 14:426–430 (1993)) than men, including both rheumatologic and non-rheumatologic autoimmune disorders. Female to male ratios of greater than 5 to 1 have been reported, for example, for scleroderma, systemic lupus erythematosus, Sjögren's syndrome, Hashimoto's thyroiditis, and primary biliary cirrhosis (Silman, *Ann. Rheum. Dis.* 50(4):887–893 (1991); Hochberg, *Arthritis Rheum.* 28:80–86 (1985); Kelly et al., *Brit. J. Rheumatol.* 30:437–442 (1991); Furszyfer et al., *Mayo Clin. Proc.* 45:586–596 (1970); and Danielsson et al., *Heptology* 11:458–464 (1990)). Numerous studies have investigated sex hormones and autoimmunity, particularly in animal models, of autoimmune disease, and some have demonstrated immunomodulatory effects of sex steroids (Grossman, *Science* 227:257–261 (1985); and Lahita, *Ann. NY Acad. Sci.* 658:278–287 (1993)). Perhaps as a result of these studies, the female predilection for autoimmune disease has sometimes been attributed to female/male differences in sex hormones. However, convincing correlations of studies in animal models with human autoimmune diseases have been limited and at least three additional observations argue against this assumption. These include the age-specific incidence patterns of different autoimmune diseases in women, contrasting effects of exogenous sex steroid administration, and contrasting effects of pregnancy.

If sex hormone levels explained the female predominance of autoimmunity, peak age-specific incidence would be expected to occur when sex hormone levels are highest. The peak incidence of systemic lupus erythematosus, at 25 to 34 years in black females (Hochberg, *Arthritis Rheum.* 28:80–86 (1985)), is consistent with this expectation. However, this age-specific incidence pattern is not the rule. For women with rheumatoid arthritis the incidence of disease continues to rise with age at least into the 8th decade of life (Hochberg, *Sem. Arthritis Rheum.* 19:294–302 (1990)), thus lacking a correlation with the time when female sex hormone levels are high. Similarly the peak incidence of Hashimoto's thyroiditis in women occurs in postmenopausal years at 50–59 (Furszyfer et al., *Mayo Clin. Proc.* 45:586–596 (1970)). A bimodal distribution is observed for women with polymyositis with peaks at 10–14 and 45–64 years (Medsger et al., *Am. J. Med.* 48:715–723 (1970)). The observation that exogenously administered sex steroids do not have similar effects on different autoimmune diseases or susceptibility to disease (Wingrave et al., *Lancet* 1:569–571 (1978); McHugh et al., Scott and Bird (eds), Oxford Univ. Press., Oxford, p. 81–113 (1990); and Grimes et al., *Am J. Obstet Gynecol.* 153:179–186 (1985)) also argues against the assumption that differences in sex hormone levels explain the general female predisposition to autoimmunity. Lastly, although sex steroid levels increase during pregnancy, pregnancy has dissimilar effects on different autoimmune diseases both with respect to modulation of existing disease (McHugh et al., supra; and Hench, *Proc. Staff Meeting Mayo Clin.* 13:161–167 (1938)), and also with respect to susceptibility to development of autoimmune disease (Grimes et al., *Am J. Obstet Gynecol.* 153:179–186 (1985); and Spector et al., *Arthritis Rheum.* 33:782–789 (1990)). Thus it is difficult to envision a mechanism by which female/male differences in sex hormone levels provide a unifying explanation for the female predilection to autoimmune disease.

Pregnancy presents an immunologic challenge to a woman since half of the genes of the fetus derive from the father. HLA genes are of particular interest since they encode molecules that are known to function as classical transplantation antigens and also govern immune responses. The trophoblast expresses HLA-G which is believed to have limited polymorphism (van der Ven et al., *J. Immunol.* 153:5628–5633 (1994)), but does not express classical HLA antigens. Nevertheless, whether by fetal cells escaping into the maternal circulation, or by other means, the mother is exposed to fetal HLA as evidenced by maternal antibodies to paternal HLA (Payne, *Arch. Intern. Med.* 99:587–606 (1957)). Moreover, maternal immune recognition of fetal HLA occurs without cost to fetal well-being, i.e., the HLA-disparate fetus escapes rejection.

Women with rheumatoid arthritis frequently experience remission of their disease during pregnancy (Hench, *Proc. Staff Meeting Mayo Clin.* 13:161–167 (1938)). In studies comparing women with arthritis remission during pregnancy to those in whom arthritis was active, an association was observed between fetal-maternal HLA class II disparity and amelioration of RA during pregnancy (Nelson et al., *N. Eng. J. Med.* 329:466–471 (1993)). In addition to presenting foreign antigens, recent studies have found that HLA molecules also present self-peptides derived from other HLA molecules (Engelhard, *Ann. Rev. Immunol.* 12:181–207 (1994)). It is therefore possible to envision a mechanism by which the presence of fetal HLA peptides could be beneficial for a woman with RA during pregnancy if autoimmunity results either from aberrant presentation, or aberrant recognition, of an HLA self-peptide. While concentrations of fetal HLA peptides high enough to result in effective direct competition at peripheral joints may be unlikely, an effect on the maternal T cell repertoire is conceivable, particularly in view of recently summarized evidence of thymic activity during pregnancy (Clarke et al., *Immunol. Today* 15:545–551 (1994)).

The beneficial effect of pregnancy on women with pre-existing RA is limited to the gestational period, and with few exceptions disease returns postpartum. Whereas the pregnancy-induced disease remission experienced by women with RA is not characteristic of other autoimmune diseases, postpartum exacerbation of RA, and also the onset of new disease, are features shared by many other autoimmune disorders, such as autoimmune thyroiditis, multiple sclerosis, myasthenia gravis and systemic lupus (Silman, *Arthritis Rheum.* 35:152–155 (1992); Jansson et al., *J. Clin. Endocrinol. Metab.* 58:681–687 (1984); Cook et al.,*Adv. Neurol.* 64:83–95 (1994); Plauche, *Clin. Obs. Gynecol.* 26:592–604 (1983); and McHugh et al., supra). Certainly, postpartum fluctuations in sex hormone levels are dramatic and might have effects on maternal immunity.

Scleroderma is a disease with female/male ratios as high as 14:1, and in which the peak age-specific incidence for women is 35–54, i.e. after child bearing years (Silman, *Ann Rheum. Dis.* 50(4):887–893 (1991)). Scleroderma, also referred to as progressive systemic scleroderma, is characterized by diffuse fibrosis, degenerative changes, and vascular abnormalities in the skin, articular structures, and internal organs, especially the esophagus, intestinal tract, thyroid, lung, heart and kidney. The disease varies in severity and progression, with its features ranging from generalized cutaneous thickening with rapidly progressive and often fatal visceral involvement, to a form distinguished by restricted skin involvement and prolonged passage of time before full manifestation of internal disease. Scleroderma bears a striking resemblance to graft-versus-host disease that occurs in some patients after bone marrow transplantation (Chosidow et al., *J. Am. Acad. Dermatol* 26:49–55 (1992); Claman, *Curr. Opin. Rheumatol* 2:929–931 (1990); Majoor et al., *J. Rheumatol* 15:1339–1345 (1988); Graham-Brown et al., *Clin. Exp. Dermatol* 8:531–538 (1983); Furst et al., *Arthritis Rheum.* 22:904–910 (1979); and Lawley et al., *Ann Int. Med.* 87:707–709 (1977)). Treatment is primarily immunosuppressive in nature, e.g., corticosteroids, colchicine or other immunosuppressive agents, which may be used in conjunction with agents which provide symptomatic relief. Prognosis is poor if cardiac, pulmonary or renal manifestations are present at time of diagnosis.

What is urgently needed is a means for treating individuals predisposed to or suffering from scleroderma or related diseases. Based on an understanding of the events which are associated with development of the disease, new methods for therapeutic or prophylactic intervention in the disease process can be devised. Quite surprisingly, the present invention addresses this and other related needs.

SUMMARY OF THE INVENTION

In one aspect the invention provides methods and compositions for inhibiting the development of scleroderma and related diseases associated with allogeneic microchimerism in an individual predisposed to or suffering therefrom. The methods comprise removing allogeneic cells from the individual being treated, where removal is meant to include physical separation from the patient or removal by causing a cytotoxic effect on the allogeneic cells. Thus, the step of removing or inhibiting the viability of allogeneic cells in the individual predisposed to or suffering from scleroderma or a related disease can be performed outside the body of said individual, such as blood cells removed from the patient and allogeneic cells separated from the heterogenous collection by positive or negative selection, e.g., by immunoaffinity chromatography or the like, or the allogeneic cells can be removed by cytotoxicity. In any event, the autologous cells or the treated autologous/allogeneic mixture can be returned to the patient. It is another feature of the invention that the method can be performed wherein the step of removing or inhibiting the viability of allogeneic cells in the individual predisposed to or suffering from scleroderma or related disease is performed in the individual, such as by administering a cytotoxin targeted to the allogeneic cells.

The targeting agent can be a monoclonal antibody or binding fragment thereof or other similarly specific molecule, directed to an HLA antigen or other antigen that distinguishes the allogeneic cells from the patient's cells, e.g., transferrin receptor, glycophorin-A or the like or other fetal cell markers. It is another feature of the invention that the treatment methods can be used in conjunction with other treatment protocols, including those conventionally used for scleroderma and related diseases, and that the treatment can be repeated over a prolonged period of time as necessary to eliminate the reoccurrence of allogeneic cells from the individual. In the case of multiple allogeneic cell types, e.g., as can be encountered in women with multiple pregnancies, a combination of targeted cytotoxic molecules (e.g., to different HLA antigens) can be employed to more effectively reduce the allogeneic cell population.

It is yet another feature of the invention that the progress of therapy can be monitored via diagnostic protocols for allogeneic cells in the patient. Moreover, the diagnostic protocols can be used to identify the alloantigens or other antigens present on the allogeneic cells and the appropriate therapy, tailored for such antigen(s), can be instituted in accordance with this information.

DESCRIPTION OF THE SPECIFIC EMBODIMENTS

The present invention provides methods for treating scleroderma and other diseases which are associated with an allogeneic microchimerism. Among these diseases are sclerodermatomyositis, mixed connective tissue disease, polymyositis/dermatomyositis, Sjogren's syndrome, primary biliary cirrhosis, and idiopathic thrombocytopenic purpura (ITP) and other collagen vascular diseases, such as systemic lupus erythematosus, multiple sclerosis, autoimmune thyroiditis, myasthenia gravis. The methods are based at least in part on the observation that an allogeneic microchimerism contributes, indirectly or directly, to susceptibility to the disease process, although the invention itself is not limited by mechanisms of pathogenesis. Thus, the methods relate to determining the presence of a microchimerism of cells from a different individual present in the individual of interest. The non-self, or allogeneic, cells eventfully contribute to the susceptibility to or development of scleroderma or related disease similar to that which occurs in graft-versus-host disease following transplantation. Some cases of graft-versus-host disease may be associated with cells from donors who have an allogeneic microchimerism. Once the microchimerism of non-self allogeneic cells is established, the development or progression of disease is inhibited by targeting the allogeneic cells for removal or inhibiting their viability.

By "allogeneic cell" is meant a cell from a genetically different member of the same species, especially with regard to alloantigens. Alloantigens are antigens that elicit an immune response when introduced into a genetically different individual of the same species. Allogeneic cells can be introduced in an individual through a wide variety of means. Most commonly, women are exposed to allogeneic cells during pregnancy. Recent advances in techniques for prenatal diagnosis in which fetal cells are detected in maternal blood samples has resulted in the surprising finding that fetal cells may persist in maternal circulation for years after pregnancy completion. In one report fetal cells were found in blood samples from women up to 27 years after pregnancy (Bianchi, *Ann. NY Acad. Sci.* 731:92–102 (1994)). In most cases these cells were identified as CD34+CD38+, representing hematopoietic stem cells capable of differentiation into the lymphoid line. In one of seven cases fetal T lymphocytes were also identified. Cells from a pregnant woman can also enter the fetus, thereby resulting in an allogeneic chimerism in individuals regardless of sex or previous pregnancies. Allogeneic cells can also be introduced through infusion of non-irradiated cells, organ or tissue transplants, etc. Studies have suggested that when the donor and recipient display homozygosity for certain HLA antigens, the donor cells may persist in the recipient individual (McMilin and Johnson, *Transfus. Med. Rev.* VII:37–43 (1993), i.e., certain HLA relationships predispose to extended microchimerism.

The presence of allogeneic cells in an individual can be determined in a wide variety of ways. Typically, in the context of the present invention a sample of cells is removed from the individual being tested for susceptibility to or potentially suffering from scleroderma or other disease associated with allogeneic microchimerism. The cell sample is most conveniently a sample of blood, but other fluids or tissues can also suffice, e.g., cellular samples of bone marrow, lymph nodes, spleen, lung, kidney, liver or other tissues and organs. The cell sample is then analyzed for the presence of allogeneic cells, typically by oligonucleotide-based or immunologic tests specific for allogeneic markers. Typically the markers are HLA markers, such as HLA antigens not associated with the individual, or the genes which encode such antigens, but other markers can also be used, such as fetal antigens (e.g., transferrin receptor (CD71), glycophorin-A), Y-chromosome markers when the individual being tested is a woman, etc. Specific monoclonal antibodies to the polymorphic HLA class I (HLA-A, B and C) or class I-like (HLA-E, -F and -G), and class II (DR, D and DP), antigens are widely described, e.g., Herzenberg et al., infra, Yeoh et al., infra, Histocompatibility Testing 1984, Albert et al., eds., Springer-Verlag (New York) (1984), EPO publication EP 204,522, ATCC Catalogue of Cell Lines and Hybridomas, 7th ed. Rockville, Md. (1992), etc.

Most techniques for detecting fetal cells in an individual have been developed using fetal nucleated red blood cells, or trophoblast cells as targets (Simpson, J. Am. Med. Assoc. 270:2357–2361 (1991)), however lymphocytes have also been detected (Bianchi, Ann NY Acad Sci. 731:92–102 (1994); Sargent et al., Ann NY Acad Sci. 731:147–153 (1994); Yeoh et al., Prenat. Diagn. 11:117–123 (1991); and Wessman et al., Prenatal Diagnosis 12:993–1000 (1992); including by means of fluorescence-activated cell sorting as described by Herzenberg et al., Proc. Natl. Acad. Sci USA 76:1453–1455 (1979), each of which is incorporated herein by reference).

Particularly preferred methods and devices for the selection of allogeneic cells, including those which are CD34-positive hematopoietic cells, are described in U.S. Pat. Nos. 5,215,927, 5,225,353, 5,262,334 and 5,240,856, each of which is incorporated herein by reference in its entirety. These patents describe methods and devices for isolating or separating target cells from a mixture of non-target and target cells, wherein the target cells are labeled, directly or indirectly, with a biotinylated antibody to a target cell surface antigen. Labeled cells are separated from unlabeled cells by, flowing them through a bed of immobilized avidin, the labeled cells binding to the avidin by virtue of the biotinylated antibody bound to their surface, while the unlabeled cells pass through the bed. After washing the bed material, the labeled (bound) cells can be eluted from the bed, for example, by mechanical agitation. A cell separator device is also provided for separating target cells from non-target cells, one embodiment being the CEPRATE SC™ cell separation system described in Berenson et al. (Adv. Bone Marrow Purging & Processings, N.Y., Wiley-Liss, 1992, pg. 449).

According to one protocol, a suspension of cells from the individual being tested is incubated with a first reagent specific for the allogeneic marker, for example, an antibody, preferably a monoclonal antibody or binding fragment thereof specific for a fetal cell marker or HLA alloantigen, as described in, e.g., Bianchi et al., Prenat. Diagn. 13:293–300 (1993), incorporated herein by reference. Complexes are formed between the targeted component and the first reagent. Unreacted first reagent is preferably removed by, e.g., a washing step. The suspension containing the complexes is then reacted with a biotinylated second reagent, selected because it has specificity for the first reagent, to associate or bind the first and second reagents and thereby form biotinylated second reagent/first reagent-allogeneic marker complexes. For example, the first reagent may be a murine monoclonal antibody specific for the marker, and the second reagent is a biotinylated anti-mouse immunoglobulin. Unreacted biotinylated second reagent can then be removed. The suspension containing the biotinylated second reagent/first reagent-marker complexes is reacted with avidin, preferably insolubilized avidin such as an avidin coated gel packed in a chromatography column, to bind the biotin and form avidin/biotinylated second reagent/first reagent-marker complexes. The remainder of the suspension is then separated from the avidin-containing complex and the presence of the allogeneic cells detected in the separated complexes. This and similar procedures are described in, e.g., U.S. Pat. No. 5,215,927, incorporated herein by reference.

The presence of allogeneic cells in an individual can also be assessed by genetic means using markers specific for suspected allogeneic cells. Representative genetic methods include in situ hybridization ("ISH"), particularly fluorescence in situ hybridization ("FISH"), and polymerase chain reaction. The use of PCR analysis and oligonucleotide probes are generally described in, e.g., Erlich et al., Arch. Pathol. Lab. Med. 117: 482–485 (1993); Gaur et al., J. Mol. Evol. 9:599–609 (1992); and Nuovo, PCR in Situ Hybridization. Protocols and Applications, Raven Press, New York, N.Y. pp 157–183 (1992), Loh et al. Science 243: 217–222, 1989; Frohman et al., Proc. Natl. Acad. Sci. USA 85: 8998–9002, 1988; Erlich (ed.), PCR Technology: Principles and Applications for DNA Amplification, Stockton Press, 1989; and U.S. Pat. No. 4,683,195, each incorporated herein by reference. Probes specific to individual donors are used not only to identify donor cells in recipient peripheral blood, but also to detect donor cells in recipient lymphoid tissue.

For example, peripheral blood or other cells obtained from a woman can be examined for the presence of male cells, detected by PCR amplification of a Y chromosome-specific (male-specific) determinant, as described in, e.g., Lucotte et al., Mol. Cell. Probes 5: 359–363 (1991), Lo et al., Lancet II: 1363–1365 (1989); Lo et al., Lancet I:335–463 (1990); and Wachtel et al., Hum. Repro. 6:1466–1469 (1990), incorporated herein by reference. PCR amplification can also be used to identify HLA sequences specific for allogeneic cells, such as to distinguish fetal cells from maternal cells or the like, as generally described in, e.g., Mueller et al., Lancet 197–200 (1990), Yeoh et al., Prenat. Diagn. 11:117–123 (1991); Tilanus, PCT publication WO 92/08117; Santamaria et al., PCT publication WO 92/19771; Versluis et al., Hum. Immunol. 38:277–283 (1993); Petersdorf et al., Tissue Antigens 44:211–216 (1994); Bell et al., Proc. Natl. Acad. Sci. USA 84:6234–6238 (1987); and Knipper et al., Tissue Antigens 44:275–284 (1994), each of which is incorporated herein by reference.

Standard in situ hybridization techniques can also be used to probe a given sample (typically a metaphase spread). Briefly, in situ hybridization comprises the following major steps: (1) fixation of cells or tissue to be analyzed by depositing cells, either as single cell suspensions or as tissue preparation, on solid supports such as glass slides and fixed by choosing a fixative which provides the best spatial resolution of the cells and the optimal hybridization efficiency; (2) prehybridization treatment of the cells or tissue to increase accessibility of target DNA, and to reduce nonspecific binding; (3) hybridization of the mixture of nucleic acids to the nucleic acid in the cells or tissue; (4) posthybridization washes to remove nucleic acid fragments not bound in the hybridization and (5) detection of the hybridized nucleic acid fragments. The reagent used in each of these steps and their conditions for use vary depending on the cell source, probe, etc. of the particular application. Several guides to the techniques are available, e.g., Gall et al. *Meth. Enzymol.* 21:470–480 (1981) and Angerer et al., in *Genetic Engineering: Principles and Methods*, Setlow and Hollaender, Eds., 7:43–65, Plenum Press, New York (1985), in addition to protocols described in Pinkel et al., *Proc. Natl. Acad. Sci. USA* 85:9138–9142 (1988), WO 93/18186, EPO Pub. No. 430,402, and Hall et al., *Blood* 84 (10 Suppl. 1): 97A (1994), each of which is incorporated herein by reference.

Once the allogeneic cells are identified in the individual susceptible to or suffering from scleroderma or a related disease, an appropriate treatment protocol can be implemented wherein the allogeneic cells are targeted for removal. Removal may comprise killing, inhibiting the ability of allogeneic cells to replicate, or physical separation from the individual being treated. As used herein, the terms "treatment," "treating" or "therapy" relate to a protocol for preventing or reducing susceptibility to scleroderma or related diseases from occurring in a subject who may be predisposed to these diseases but who has not yet been diagnosed as having them; inhibiting these diseases, i.e., arresting their development; or ameliorating or relieving the symptoms of these diseases, i.e., causing regression of a scleroderma disease state or other disease associated with allogeneic microchimerism.

The treatment of the invention is directed to removal of allogeneic cells from the individual of interest. Removal can be performed in vivo or ex vivo. In the case of in vivo treatment, one or more agents selective for the allogeneic cells are administered to the patient, which agents result in the killing, inhibition or other removal of the allogeneic cells of interest. In ex vivo treatment, a heterogenous mixture of cells is removed from the patient, allogeneic cells treated (e.g., removed via positive or negative selection, or treated in a manner that results in their inhibition or cell death), and the autologous cells are then typically returned to the patient.

Agents useful for treatment include those which are selective for allogeneic cells in an individual being treated, such as monoclonal antibodies directed to an epitope of an alloantigen that distinguishes the allogeneic cells from the patient's cells, or can be made selective by conjugation to an appropriate carrier, such as a monoclonal antibody or binding fragment thereof. The monoclonal antibody or binding fragment can be cytotoxic itself, or it can be linked to a cytotoxic agent. Thus, the monoclonal antibody or binding fragment serves to target the coupled cytotoxic molecule to allogeneic cells for a desired therapeutic (or, in some cases, diagnostic) effect.

Among the cytotoxic molecules which can be targeted by the monoclonal antibodies, binding fragments thereof, or other specific binding agents are active chemotherapeutic agents, prodrugs, cytotoxins, inhibitory peptides, cytokines, enzymes, biological response modifiers, and other monoclonal antibodies or binding fragments thereof, including catalytic antibodies. The monoclonal antibodies, when of the IgG isotype, can be coupled to themselves to form homodimers and trimers and hence possess increased binding avidity in a manner similar to IgM molecules. Alternatively, the monoclonal antibodies may be conjugated to antibodies of other binding specificities, such as immune modulating antibodies and those which bind to T lymphocyte antigens, via chemical or recombinant means, to form heterodimers or hybrid (bi-specific) antibodies having a desired activity against allogeneic and effector cells.

Examples of monoclonal antibody-radionuclide conjugates which can be used in therapy include antibodies coupled to radionuclides such as $^{131}I$, $^{90}Y$, $^{105}Rh$, $^{47}Sc$, $^{67}Cu$, $^{212}Bi$, $^{211}At$, $^{188}Re$, $^{109}Pd$, $^{47}Sc$, $^{212}Pb$, $^{153}Sm$, and the like, as described in (Gansow, *Int. J. Rad Appl. Instrum.* [B], *Nucl. Med. Biol.* 18:369–381 (1991)), which is incorporated herein by reference.

For use in the present invention monoclonal antibodies can also be coupled to conventional chemotherapeutic agents to achieve substantially higher levels of the drug at the allogeneic cells. Accordingly, drugs which may possess prohibitive levels of toxicity to non-allogeneic cells may be administered at lower levels when conjugated to monoclonal antibodies or binding fragments specific for allogeneic cells. Cytotoxic drugs which may be coupled for targeting include those such as doxorubicin, cyclophosphamide, cisplatin, adriamycin, estramustine, fluorouracil, ethinyl estradiol, mitoxantrone, methotrexate, taxol, and megestrol. Methods of coupling may be direct via covalent bonds, or indirect via linking molecules, and will generally be known in the art for the particular drug selected. See, e.g., co-pending application USSN 08/454,651, and Thorpe et al., *Immunological Rev.* 62:119–158 (1982), both of which are incorporated herein by reference. The drugs may also be enclosed in liposomes which are then targeted to the allogeneic cell sites by the monoclonal antibodies which are incorporated into the liposome membranes. A wide variety of methods for preparing liposomes filled with cytotoxic drugs and which are targeted by monoclonal antibodies are generally known, and are described in, for example, U.S. Pat. Nos. 4,235,871, 4,501,728, 4,837,028, 4,957,735 and 5,019,369, each of which is incorporated herein by reference.

In another method the drug may be a prodrug and the monoclonal antibody of the invention is coupled to an enzyme which converts the prodrug to more active drug at the allogeneic cells. In this method a monoclonal antibody specific to an allogeneic cell is linked to an enzyme which is capable of converting a prodrug into a more cytotoxic drug. When introduced into the patient or heterogeneous cell collection the antibody component of the conjugate directs the conjugate to the site of the allogeneic cells and binds thereto. A prodrug that is a substrate for the enzyme is then introduced into the host and is converted by the enzyme at the site into an active cytotoxic drug. Representative drugs and enzymes useful in this method are discussed in U.S. Pat. No. 4,975,278, which is incorporated herein by reference.

Other cytotoxic binding proteins useful in the methods of the present invention are produced by fusing a cytotoxic domain and antigen binding domain derived from the monoclonal antibodies specific for allogeneic cell markers. A variety of cytotoxic molecules are suitable for use as the cytotoxic domain in such immunotoxins. Any toxin known to be useful as the toxic component of an immunotoxin may be used, preferably a protein toxin that may be recombinantly expressed. Particularly useful as the cytotoxic domain are bacterial toxins such as Pseudomonas exotoxin A (PE), diphtheria toxin, shiga toxin and shiga-like toxin, and ribosome inactivating toxins derived from plants and fungi, including ricin, a-sarcin, restrictotocin, mitogellin, tricanthosin, saporin-G, saporin-1, momordin, gelonin, pokeweed antiviral protein, abrin, modeccin and others described in *Genetically Engineered Toxins*, ed. A. Frankel, Marcel Dekker, Inc. (1992), incorporated by reference herein; and any recombinant derivatives of those proteins. See generally, Olsnes and Pihl, *Pharmac. Ther.* 25:355–381 (1982) and U.S. Pat. Nos. 4,675,382 and 4,894,443, which are incorporated by reference herein. Also useful as cytotoxic agents coupled to agents for targeting to allogeneic cells are mammalian derived (preferably human) proteins with ribonucleolytic activity, such as ribonucleases engineered to be potent cytotoxins.

The toxin molecules may be fused to, or otherwise bound to a monoclonal antibody or other allogeneic cell targeting molecule by methods generally known and available to those in the art. The two components may be chemically bonded together by any of a variety of well known chemical procedures, e.g., linkage by way of heterobifunctional cross-linkers, e.g. SPDP, carbodiimide, glutaraldehyde, or the like, or by fusion by recombinant means. See for example Sambrook et al., *Molecular Cloning: A Laboratory Manual*, Cold Spring Harbor Laboratory Press, Cold Spring Harbor, N.Y. (1989), incorporated herein by reference. The recombinant production of various immunotoxins is well-known within the art and can be found, for example in Thorpe et al., *Monoclonal Antibodies in Clinical Medicine*, pp. 168–190 Academic Press, N.Y. (1982), and Pastan et al., *Ann. Rev. Biochem.* 61:331–354 (1992)), which are incorporated herein by reference. The cytotoxins for use in the invention may be altered to have differing properties of affinity, specificity, stability and toxicity that make them particularly suitable for various clinical or biological applications as described herein. Such modifications can include an appropriate carboxyl terminal sequence to a toxin molecule to help translocate the molecule into the cytosol of targeted allogeneic cells. Amino acid sequences which have been found to be effective include, REDLK, REDL or KDEL, repeats of those, or other sequences that function to maintain or recycle proteins into the endoplasmic reticulum. See, for example, Chaudhary et al., *Proc. Natl. Acad. Sci. USA* 87:308–312 (1990) and Seetharam et al., *J. Biol. Chem.* 266: 17376–17381 (1991), incorporated by reference herein.

The targeting molecules and cytotoxic conjugates thereof which bind to the allogeneic cells can be employed in pharmaceutical compositions for uses related to treatment and diagnosis of scleroderma and diseases related to allogeneic microchimerism. The pharmaceutical compositions are intended for parenteral, topical, oral, or local administration for treatment or for in vivo diagnostic use, and can be employed in ex vivo treatments as well. Preferably, the pharmaceutical compositions are administered parenterally, i.e., intravenously, subcutaneously, or intramuscularly. The concentration of the targeting molecule and cytotoxin which binds to the allogeneic cell specific antigen can vary widely, i.e., from less than about 0.5%, usually at or at least about 1% to as much as 15 or 20% by weight and will be selected primarily by fluid volumes, viscosities, etc., in accordance with the particular mode of administration selected. Actual methods for preparing parenterally administrable compounds will be known or apparent to those skilled in the art and are described in detail in, for example, Remington's Pharmaceutical Science, 17th ed., Mack Publishing Company, Easton, Pa. (1985), which in incorporated herein by reference.

Determination of an effective amount of therapeutic agent sufficient to inhibit the allogeneic cells may be determined by, for example, monitoring the presence of allogeneic cells with a variety of procedures, e.g., in vivo imaging or ex vivo diagnostic techniques, as described herein. The therapeutic compositions are administered to a patient already suffering from or susceptible to scleroderma or related disease in an amount sufficient to cure or at least partially arrest the disease or inhibit its development or a predisposition thereto. An amount adequate to accomplish this is defined as "therapeutically effective dose." Amounts effective for this use will depend on the stage and severity of the disease and its location, and the weight and general state of the patient being treated, but generally range from about .01 mg/kg to about 100 mg/kg host body weight of an immunotoxin per day, with dosages of from about 0.1 mg/kg to about 10 mg/kg per day being more commonly used. Maintenance dosages over a prolonged period of time may be adjusted as necessary. It must be kept in mind that the materials of the present invention may be employed in serious disease states, that is, life-threatening or potentially life threatening situations. In such cases, in view of the minimization of extraneous substances and general lack of immunogenicity, especially when a human or substantially human monoclonal antibody is employed in an immunoconjugate to treat human hosts, it is possible and may be felt desirable by the treating physician to administer substantial excesses of these compositions.

Single or multiple administrations of the compositions can be carried out with the dose levels and pattern being selected by the treating physician. In any event, the pharmaceutical formulations should provide a quantity of the cytotoxic sufficient to effectively inhibit allogeneic cells associated with the disease. The pharmaceutical compositions may be administered alone or in methods of adjunct therapy, e.g., with corticosteroids or other agents, such as D-penicillamine, colchicine and other immunosuppressive agents, vasodilators, dialysis and transplantation. When administered as adjunct therapy, the compositions of the present invention may be administered concurrently with the other treatment modalities, or separately at different intervals.

The therapeutic methods of the invention can also be performed ex vivo, i.e., outside the body. For example, blood cells or other heterogeneous target cell population are removed from a patient and the allogeneic cells separated therefrom, as described herein, or treated with allogeneic-specific cytotoxic agents, e.g., monoclonal antibodies conjugated to cytotoxic agents such as toxins, drugs, labels, etc., proving a therapeutic concentration of the compositions far in excess of levels which could be accomplished or tolerated by the patient. Following treatment to eliminate the allogeneic cells in the target cell population or tissue, the cells or tissues may be returned to the patient.

In another aspect of the invention, allogeneic cells are detected by diagnostic imaging to monitor progress of the patient, particularly in association with the therapy described herein. For example, by associating an imageable label with a monoclonal antibody or binding fragment specific for an allogeneic cell marker, such as transferrin receptor or glycophorin-A, an image of the site(s) of allogeneic cell-associated disease may be obtained. The images may be used for detection of disease sites, in evaluating and monitoring therapy, or in guiding surgical removal of disease sites. Conventional diagnostic imaging techniques may be employed, as are generally known in the art. Briefly, a monoclonal antibody is labeled, such as a radiolabel, and administered to a patient in an amount sufficient to deliver an adequate supply of labeled monoclonal antibody (or binding fragment thereof) to the targeted tissues so as to permit an image to be generated. The label provides the imaging input, while the coupled (labeled) monoclonal antibody provides the targeting capability of the radiolabeled unit. Labels useful in the present invention include radionuclides such as gamma-emitters and positron emitters, and fluorescence emitters. The presence of allogeneic cells can also be detected for monitoring therapy or the like in a cellular sample obtained from a patient, i.e., ex vivo diagnosis. The detecting label may be any of the readily known labels appropriate for in vitro diagnostic determinations, such as fluorescers, chemiluminescers, enzymes, radionuclides, dye particles, etc.

All publications, patents and patent applications mentioned in this specification are herein incorporated by reference into the specification to the same extent as if each individual publication was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for diagnosing a predisposition to developing or suffering from disease, other than graft-versus host disease, associated with allogeneic cellular microchimerism in an individual, comprising:

removing a sample of cells from said individual; and determining whether said sample contains allogeneic cells, the presence of which thereby establishing said predisposition to developing or suffering from said disease.

2. The method of claim 1, further comprising, before said determining step, the step of enriching the sample of cells removed from the individual for stem cells or fetal cells.

3. The method of claim 1, wherein the enrichment for stem cells or fetal cells is performed by immunoaffinity chromatography.

4. The method of claim 1, wherein the individual is female and determining whether said sample contains allogeneic cells is by probing for polynucleotide sequences specific for the Y gene in the sample.

5. The method of claim 4, wherein the probing for polynucleotide sequences specific for the Y gene is performed by polymerase chain reaction.

6. The method of claim 1, wherein determining whether said sample contains allogeneic cells is by HLA typing.

7. The method of claim 1, wherein the sample of cells is obtained from the blood of said individual.

8. The method of claim 1, wherein the sample of cells is obtained from the lung of said individual.

9. The method of claim 1, wherein the disease associated with the allogeneic cellular microchimerism is scleroderma.

* * * * *